United States Patent [19]

Letelier et al.

[11] 4,017,502
[45] Apr. 12, 1977

[54] PROCESS FOR PURIFYING THE MIXED ESTER, ETHYLENE GLYCOL 1-(2-p-CHLOROPHENOXY)-2-METHYL-PROPIONATE NICOTINATE

[75] Inventors: Carlos Sunkel Letelier; Fernando CilleroGrafulla, both of Madrid, Spain

[73] Assignee: Alter, S.A., Madrid, Spain

[22] Filed: Aug. 4, 1975

[21] Appl. No.: 601,866

[30] Foreign Application Priority Data

June 4, 1975 Spain .................................. 438246

[52] U.S. Cl. .......................... 260/295.5 R; 424/266
[51] Int. Cl.$^2$ ....................................... C07D 213/55
[58] Field of Search ............................ 260/295.5 R

[56] References Cited

UNITED STATES PATENTS 3,622,587 11/1971 Carlson et al. ............. 260/295.5 R
3,723,446 3/1973 Scherm et al. .............. 260/295.5 R Primary Examiner—Alan L. Rotman
Attorney, Agent, or Firm—Ladas, Parry, Von Gehr, Goldsmith & Deschamps

[57] ABSTRACT

The present invention is concerned with purifying the mixed ester, ethylene glycol 1-/2-(p-chlorophenoxy)-2-methylpropionate/-2-nicotinate by passing said compound in oily form through a layer of Super-Cel and charcoal and then crystallizing said compound from a mixture of benzene/petroleum ether. This compound has hypolipidemic properties.

1 Claim, No Drawings

PROCESS FOR PURIFYING THE MIXED ESTER, ETHYLENE GLYCOL 1-(2-P-CHLOROPHENOXY)-2-METHYLPROPIONATE NICOTINATE

Various processes exist for preparing the mixed ester, ethylene glycol 1- [2-(p-chlorophenoxy)-2-methylpropionate]-2-nicotinate, of the formula:

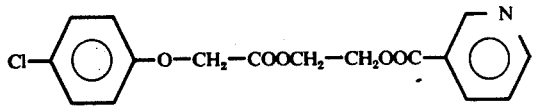

This compound, which has hypolipidemic properties, is prepared with a high yield, but in the form of an oily product boiling at 214° C/03 mm, with decomposition. A method of purifying this oily product has now been discovered, by means of which it is converted into a solid compound having a melting point of 51° C.

The purification process comprises passing the oily product prepared by the process described in U.S. patent application Ser. No. 570,529 through a layer composed of Super-Cel and charcoal. Super-Cel is the trade name for diatomaceous earth products used as filter aids. The thus purified oil solidifies at room temperature. This solid melts at 45°–48° C., and, once it has been recrystallized from benzene/petroleum ether, it melts at 51° C.

Analysis calculated for $C_{18}H_{18}ClNO_5$: C: 59.43%; H: 4.99%; Cl: 9.75%; N: 3.85%. Found: C: 59.34%; H: 4.77%; Cl: 9.78%; N: 3.68%.

EXAMPLE 200 g of the oily product are passed through a cylindrical filter 4 cm in diameter containing a 2 cm high bottom layer of Super-Cel and an 8 cm high top layer of charcoal. Passage of the oil is promoted when a pressure of 1 kg/cm² is applied and the temperature is maintained at 60° C.

The thus purified oil becomes solid at room temperature, and is optionally recrystallized from benzene/petroleum ether, whereby a white solid is obtained having a melting point of 51° C. The yield of this operation is practically quantitative.

For pharmacological use of the compound on account of its hypolipidemic properties, it can be encapsulated according to the following formulation:

| | |
|---|---|
| ethylene glycol 1-[2-(p-chlorophenoxy)-2-methylpropionate[-2-nicotinate | 300 mg |
| Aerosil 200 | 30 mg |

In conclusion, we claim:
1. A process for purifying the mixed ester, ethylene glycol 1-[2-(p-chlorophenoxy)-2-methylpropionate]-2-nicotinate, which process comprises passing said ethylene glycol 1-[2-(p-chlorophenoxy)-2-methylpropionate]-2-nicotinate prepared in oily form with the temperature maintained at 60° C. through a layer of Super-Cel and charcoal, to prepare the same compound in solid form, which is then recrystallized from benzene/petroleum ether.

* * * * *